United States Patent [19]
Johnson, III et al.

[11] Patent Number: 5,804,737
[45] Date of Patent: Sep. 8, 1998

[54] U-BOLT TESTING APPARATUS

[75] Inventors: Carl Edward Johnson, III, Columbia City; Nick Carl Knappenberger, Fort Wayne, both of Ind.

[73] Assignee: McCoy Bolt Works, Inc., Fort Wayne, Ind.

[21] Appl. No.: 921,118

[22] Filed: Aug. 29, 1997

[51] Int. Cl.⁶ .................................................. G01N 3/22
[52] U.S. Cl. ........................................ 73/761; 73/862.23
[58] Field of Search ....................... 73/761, 760, 862.23, 73/862.392

[56] References Cited

U.S. PATENT DOCUMENTS

| | | |
|---|---|---|
| 2,228,589 | 1/1941 | Backes . |
| 3,354,705 | 11/1967 | Dyer, Jr. . |
| 3,965,778 | 6/1976 | Aspers et al. . |
| 3,974,685 | 8/1976 | Walker ...................................... 73/761 |
| 4,023,406 | 5/1977 | Benz, Jr. ................................... 73/761 |
| 4,104,778 | 8/1978 | Vliet ......................................... 73/761 |
| 4,558,599 | 12/1985 | Sacks . |
| 4,715,211 | 12/1987 | Lehoczky . |
| 5,161,564 | 11/1992 | Bolton et al. ............................. 73/761 |
| 5,343,785 | 9/1994 | Holt et al. . |
| 5,492,019 | 2/1996 | Madden . |

*Primary Examiner*—Max H. Noori
*Attorney, Agent, or Firm*—George Pappas

[57] ABSTRACT

A U-bolt testing apparatus includes a pair of motors coupled to and selectively driving a pair of spindles. The spindles include sockets which are selectively movable vertically and horizontally as may be desired and which are placed over the U-bolt nuts. A U-bolt to be tested is placed on the chassis table with the component parts that are to be retained or clamped within the U-bolt and the U-bolt characteristics are tested by advancing the nuts onto the U-bolt threaded ends. In the alternative, a holding fixture is provided for securely retaining the U-bolt during testing. U-bolts having various different shapes and length of legs can be accommodated and tested by the apparatus. A computer controls the torque of the motors and nuts being advanced on the U-bolt threaded ends and monitors strain gauges which are attached to the U-bolt legs. The test data and characteristics of the tested U-bolts are viewable on an output module connected to the computer.

19 Claims, 1 Drawing Sheet

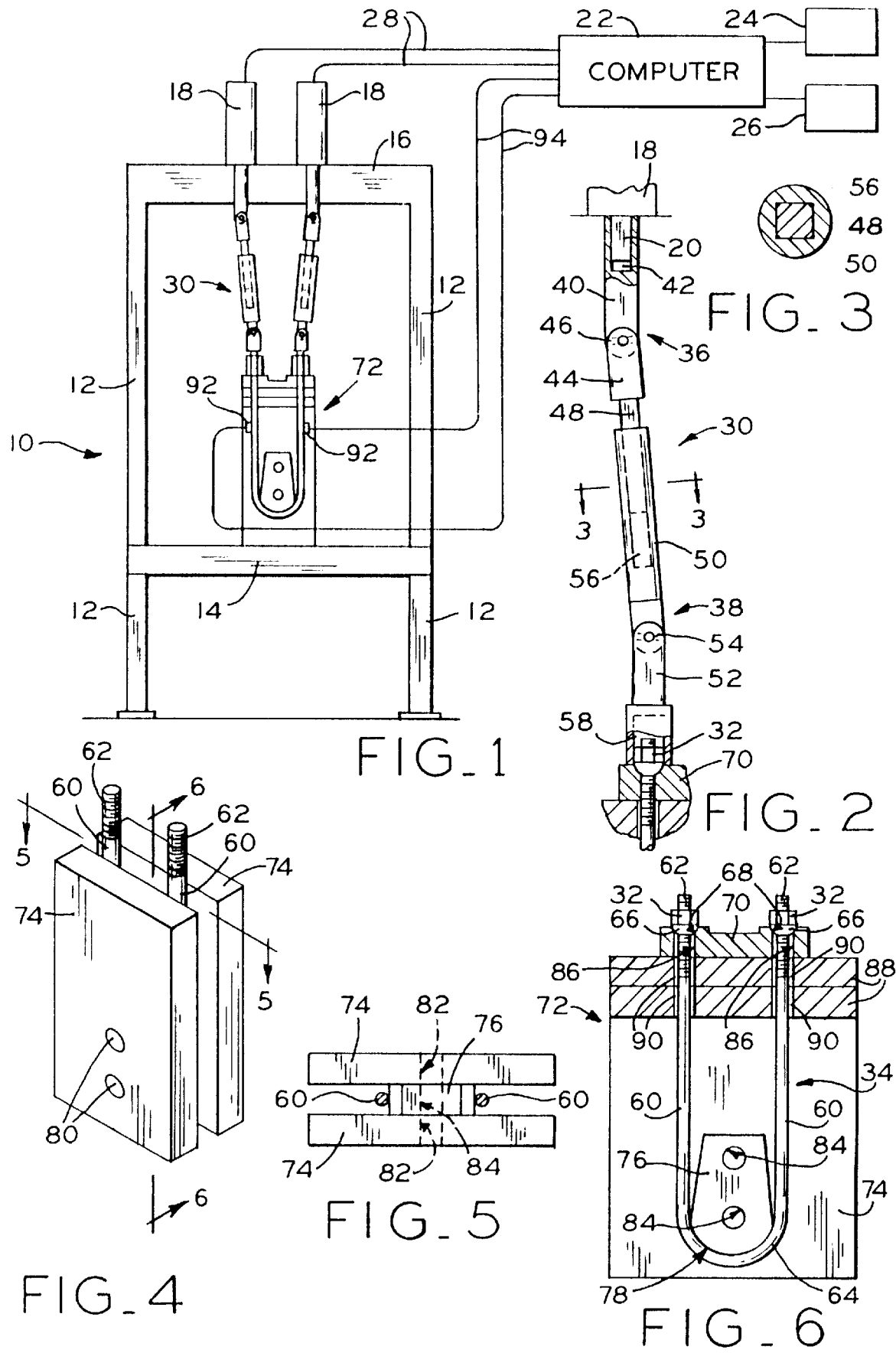

U-BOLT TESTING APPARATUS

TECHNICAL FIELD

The present invention relates to the technical field of apparatus for testing U-bolts. More specifically, the present invention relates to a U-bolt testing apparatus for determining the stress/strain seen by various configurations and sizes of U-bolts upon simultaneously applying a controlled variable dynamic torsional load, allowing for the determination of the optimal torque of the advancing U-bolt nuts onto the threaded ends of the tested U-bolt.

BACKGROUND OF THE INVENTION

U-bolts have and are extensively used as fasteners for various different component parts. For example, some of the larger U-bolts are quite often used for attaching axle assemblies onto a vehicle chassis. In applications such as this, as well as many other different applications, it is desirable to advance the nuts on the threaded ends of the U-bolt legs in a manner whereby the time of assembly is minimized while, nevertheless, the proper torque and tension is achieved on the U-bolt legs.

Many different U-bolt designs currently exist having different characteristics. For example, U-bolts vary in the length of their legs, the distance between the legs, the shape of the U-bolt section located between the legs, diameter or cross sectional shape of the legs, materials of the U-bolt, thread pitch and type on the legs threaded ends, etc. All of these characteristics, along with the compressive characteristics of the components to be retained by the U-bolt, should be taken into consideration for determining the proper torque at which the nuts are advanced onto the U-bolt legs threaded ends. Unfortunately, it is nearly impossible to accurately predict the performance of any given U-bolt solely on its visible characteristics. Accordingly, a need exists for an apparatus wherein different shaped U-bolts may be tested and whereby the optimal torque used for nut advancement of any given U-bolt may more accurately, easily, quickly and inexpensively be determined.

SUMMARY OF THE INVENTION

It is the principal object of the present invention to overcome the above-discussed disadvantages associated with determining the characteristics of a U-bolt and to provide an apparatus whereby U-bolts may easily, quickly and inexpensively be tested for accurately determining at least the optimal torque for advancing the nuts on the U-bolt legs threaded ends. The objects of the present invention are accomplished by providing an apparatus for testing U-bolts including a chassis having a table upon which the U-bolts are placed when tested and an upper support whereat a pair of motors are provided. The motors are preferably hydraulic motors operating and driven by high pressure hydraulic fluid. Each of the motors include an output rotatably driven shaft. The pressure and flow of the hydraulic fluid to the motors are controlled by a computer which, therefore, controls the torque and rotational speed of the motor output shafts. A set of spindles are provided each of which extend between the motor output shafts and are coupled to a U-bolt nut. The spindles effectively transfer the rotational forces of the motor output shafts to wherever the U-bolt nuts may be located for any given U-bolt being tested. Each of the spindles include an upper section. The upper sections include an extension coupling shaft which is effectively pivotally connected to a motor output shaft with a universal joint. The spindles each further include a lower section each of which comprise a nut socket pivotally connected by another universal joint to a sleeve. The extension coupling shaft of the upper section is selectively longitudinal received within a bore located in the sleeve of the lower section. Thus, spindle structure allows the placement of the nut socket at many different locations as may be desired and needed for testing different shaped U-bolts.

The interconnections between the motor output shafts and the U-bolt nuts, whether or not including universal joints, an extension coupling shaft, a sleeve having a bore for receiving the coupling shaft, a nut socket, etc., are referred herein as spindles. These spindles effectively transfer the rotational motion and torque from the motor output shafts to the U-bolt nuts. In the preferred embodiment wherein the spindles include an extension coupling shaft and a sleeve with a coupling shaft receiving bore, both the coupling shaft and the sleeve receiving bore are square shaped in cross section so that the coupling shaft and sleeve are selectively longitudinally movable with respect to one another but the rotational forces of the coupling shaft are transferred to the sleeve. Accordingly, the nut socket is movable to any number of different positions both horizontally and vertically for advancing the nuts of various different size and shapes of U-bolts.

A holding fixture is provided for placing on the chassis table and for securely retaining a U-bolt while the nuts are treadingly advanced onto the U-bolt threaded ends and while the U-bolt is being tested. The holding fixture includes a set of plates which sandwich the U-bolt. A stop member is located within the U-bolt inbetween the U-bolt legs and is also sandwiched between the fixture plates. The stop member is retained in position with one or more pins that extend through aligned holes in the plates and the stop member. At the upper end of the holding fixture plates, there is provided a cap having a pair of holes therethrough for receiving the U-bolt threaded ends. Thus, by treadingly advancing the nuts on the U-bolt threaded ends toward the cap, the U-bolt legs are placed in tension. One or more spacers are provided and are selectively located between the holding fixture plates and the cap so that U-bolts with various different lengths of legs and/or threaded ends may be tested.

In addition to the computer controlling the torque of the motors, the computer is connected to and monitors strain gauges which are affixed to the U-bolt legs. The computer records the torque of the motors as well as the outputs of the strain gauges and provides a visual output to the operator which therefore represents the characteristics of the U-bolt. For obtaining the most accurate characteristics of a U-bolt in any given application, rather than using the U-bolt holding fixture, the actual components to be fastened by the U-bolt are placed on the chassis table and the U-bolt is tested directly thereon. In this manner, the compression characteristics of those components are also taken into consideration for determining the optimal torque at which the nuts should be rotated so as to achieve the optimal clamping force while preventing overtorquing or otherwise damaging the U-bolt structure.

In one form thereof, the present invention is directed to an apparatus for testing U-bolts having a U-shaped body, legs having threaded ends, and a nut on each of the threaded ends. The U-bolt testing apparatus includes a pair of motors, each having an A output rotatably driven shaft. A pair of spindles are provided, each one of the spindles extending between one of the rotatably driven motor shafts and one of a pair of nuts which are threadingly received on a threaded end of a U-bolt. The pair of motors are selectively simultaneously driven for selectively simultaneously rotatably driving the pair of spindles and the U-bolt nuts, thereby selectively simultaneously threadingly advancing the U-bolt nuts on the threaded ends.

BRIEF DESCRIPTION OF THE DRAWINGS

The above-mentioned and other features and objects of this invention and the manner of obtaining them will become more apparent and the invention itself will be better understood by reference to the following description of embodiments of the invention taken in conjunction with the accompanying drawings wherein:

FIG. 1 is a front elevation view of a U-bolt testing apparatus constructed in accordance with the principles of the present invention;

FIG. 2 is a partial elevation view of a spindle connection between a motor output shaft and U-bolt nut shown in FIG. 1;

FIG. 3 is a cross-sectional view taken generally along line 3—3 of FIG. 2;

FIG. 4 is a partial perspective view of the holding fixture used in the U-bolt testing apparatus shown in FIG. 1;

FIG. 5 is a cross-sectional view taken generally along line 5—5 in FIG. 4; and,

FIG. 6 is a cross-sectional view taken generally along line 6—6 in FIG. 4.

Corresponding reference characters indicate corresponding parts throughout the several views of the drawings.

The exemplifications set out herein illustrate preferred embodiments of the invention in one form thereof and such exemplifications are not to be construed as limiting the scope of the disclosure or the scope of the invention in any manner.

DESCRIPTION OF THE PREFERRED EMBODIMENTS

Referring initially to FIG. 1, a U-bolt testing apparatus constructed in accordance with the principles of the present invention is shown and designated by the numeral 10. U-bolt testing apparatus 10 includes a frame or chassis made up of upright members 12, table 14, and an upper support 16.

Apparatus 10, further includes a pair of motors 18 mounted upon upper support 16. Each motor 18 has an output rotatably driven shaft 20. Motors 18 can be one of many different types including electric (direct current or alternating current) and hydraulic. Preferably, motors 18 are hydraulic motors which are operated and driven by high pressure hydraulic fluid delivered to motors 18 by high pressure fluid lines (not shown).

The torque of each of motors 18 are individually controlled by a computer 22 as may be desired by the operator. Computer 22 includes an input module 24, preferably a keyboard and an output module 26, preferably a monitor or cathode ray tube (CRT). The flow and pressure of hydraulic fluid to motors 18 is controlled via hydraulic valves (not shown) which are monitored and selectively controlled by the computer 22 via electronic control lines or wires 28. Accordingly, the operator selectively controls the torque of motor output shafts 20 by imputing the desired criteria into the input module 24. The operator may also view the actual performance of motors 18 on the output module 26.

A pair of spindles 30 are provided between each of motor shafts 20 and nuts 32 of a U-bolt 34. Referring now more specifically to FIGS. 2 and 3, each of spindles 30 include an upper section 36 attached to and extending from the motor shafts 20 and a lower section 38 extending between the upper section 36 and the U-bolt nut 32. The upper section 36 includes a motor coupling section 40 having a bore 42 for receiving a motor shaft 20. Motor shaft 20 is attached to the motor coupling section 40 by screws and/or a keyway and key (not shown) or in other ways customary in the trade. An extension coupling shaft 44 is pivotally attached to the motor coupling section 40 via a universal joint 46. Universal joint 46 allows the extension coupling shaft 44 to pivot with respect to the motor coupling section 40 in the two horizontal axes of rotation in a known and customary manner. Extension coupling shaft 44 includes a lower extension 48 which, as best seen in FIG. 3, is square shaped in cross section.

The lower section 38 of spindles 30 include a sleeve member 50 pivotally connected to a nut socket member 52 via a universal joint 54. Similar to universal joint 46, universal joint 54 allows the nut socket member 52 to pivot about both horizontal axes of rotation in a known and customary manner with respect to the sleeve member 50. The nut socket member 52 includes a hexagonal socket or bore 58 adapted to be received snugly over the U-bolt nut 32. At the other end of the lower section 38, the sleeve member 50 is provided with a coupling shaft receiving bore 56 which, as best seen in FIG. 3, is also square shaped in cross section. Receiving bore 56 is slightly larger than the lower extension 48 and, therefore, the lower extension 48 of the upper section 36 is selectively longitudinally received within the receiving bore 56 of the lower section 38. Thus, as can now be appreciated, the nut socket member 52 is selectively movable both vertically and horizontally in numerous different positions as desired for placement over a U-bolt nut 32. Further, the lower sections 38 of spindles 30 are selectively removable from the position shown in FIG. 2 by merely lifting the socket member 52 up and over the U-bolt nut 32 and sliding the entire lower section 38 downwardly for removing the lower extension 48 from within the receiving bore 56. Nevertheless, in the position as shown in FIG. 2, the spindles 30 effectively transfer the rotational forces of the motor shafts 20 down to the nut socket members 52 and thereby selectively turn the nuts 32 clockwise or counterclockwise as may be desired.

U-bolts which may be tested by the apparatus 10, such as U-bolt 34, typically include legs 60 terminating in threaded ends 62. U-bolts 34 typically also include a circular, square or other shaped interconnection 64 extending between and connecting the legs 60. Nuts 32 are selectively threadingly received on threaded ends 62 as shown in a known and customary manner. Nuts 32 may also include a lower dome shaped surface area 66 adapted to mate and fit within a dome shaped recess 68 located on the cap 70 or other component parts upon which the nuts 32 may selectively be caused to advance upon.

For testing a U-bolt 34, preferably, the actual component parts which are to be retained by the U-bolt are placed within the U-bolt and all such components and U-bolt are placed on the table 14 for testing. During such testing, the nut socket members 52 are selectively moved as described hereinabove wherever needed for placing over the nuts 32 of that particular assembly of component parts and testing is, thereafter, conducted as may be desired.

In the event that the actual component parts are not available for testing of the U-bolt 34 or testing is desired without taking into consideration the component parts to be retained by the U-bolt, a holding fixture generally designated by the numeral 72 is provided for securely retaining the U-bolt 34 during testing. Holding fixture 72 includes a set of plates 74 adapted to sandwich a U-bolt 34 therebetween as shown in FIG. 4. Plates 74 are adapted to set on table 14 and may be secured thereon if desired by various fastening means. Plates 74 may also be secured to one another by various fastening means. Holding fixture 72 further includes a stop member 76 located and also sandwiched between plates 74. Stop member 76 includes a lower surface area 78 shown in FIG. 6 as being circular so as to accommodate the U-bolt interconnection shape 64. The lower surface area 78 of stop member 76 can however be shaped in many different configurations for accommodating the different shaped interconnections 64 of the U-bolt 34. Stop member 76 is retained in the position shown in FIG. 6 and between the plates 74 via a set of pins 80 which are selectively received through aligned holes 82 in plate 74 and holes 84 in the stop member 76.

For testing a U-bolt 34, the U-bolt is merely placed inbetween the plates 74 with the stop member 76 also inbetween the plates 74 and within U-bolt 34. Stop member 76 is secured in position by placing pins 80 in respective aligned holes 82 and 84. The cap 70 is placed over and on top of plates 74 as shown with the threaded ends 62 of U-bolt 34 extending through holes 86 of cap 70. It is noted that holes 86 communicate with the dome shaped recesses or bores 68 of cap 70 as shown. Thereafter, the nuts 32 are first threadingly placed on the threaded ends 62 of U-bolt 34 by hand and the nut socket members 52 are placed thereover as shown in FIGS. 1 and 2. As also discussed hereinabove, the nuts 32 are selectively advanced onto the threaded ends 62 by selectively turning the spindles 30 as may be desired.

For accommodating different lengths of legs 60 of U-bolt 34, one or more spacers 88 may be provided between the cap 70 and plates 74. As best seen in FIG. 6, spacers 88 include holes 90 wherethrough the threaded ends 62 and legs 60 of the U-bolt 34 are received. It is noted that various different thicknesses of spacers 88 may also be provided for selectively locating the cap 70 at a desired vertical location with respect to the overall lengths of legs 60 of U-bolt 34.

Prior to testing each U-bolt 34, a set of strain gauges 92 are affixed to each of the legs 60 of U-bolt 34 as shown in FIG. 1. Strain gauges 92 are connected to the computer 22 via electronic input wires of lines 94. Computer 22 monitors the electronic outputs of strain gauges 92 and records the output thereof as may be desired. The torque of the nuts 32 along with the strain on the legs 60, as well as other possible inputs and outputs, are monitored and recorded by the computer 22 and are then viewed by the operator on the output module 26.

Finally, it is noted that chassis 12 as well as the various components described hereinabove making up the spindles 30 and the holding fixture 72 are preferably made of steel or other suitable materials known to one skilled in the art.

While the invention has been described as having specific embodiments, it will be understood that it is capable of further modifications. This application is, therefore, intended to cover any variations, uses, or adaptations of the invention following the general principles thereof and including such departures from the present disclosure as come within known or customary practice in the art to which this invention pertains and fall within the limits of the appended claims.

What is claimed is:

1. An apparatus for testing U-bolts having a U-shaped body, a pair of legs having threaded ends and a nut on each of said threaded ends, said apparatus comprising:

a pair of motors, each motor having an output rotatable driven shaft;

a pair of spindles, each one of said spindles extending between one of said rotatably driven motor shafts and one of a pair of nuts threadingly received on a threaded end of a U-bolt;

wherein at least one of said spindles includes a pair of universal joints whereby a nut may threadingly be advanced on a U-bolt threaded end which is not collinear with said rotatably driven motor shaft; and, wherein said pair of motors are selectively simultaneously driven for selectively simultaneously rotatably driving said spindles, and wherein said U-bolt nuts are selectively simultaneously threadingly advanced on said U-bolt threaded ends.

2. The U-bolt testing apparatus of claim 1, further comprising a holding fixture for securely retaining a U-bolt during testing.

3. The U-bolt testing apparatus of claim 2, wherein one of said universal joints is attached between a rotatably driven motor shaft and an extension coupling shaft and said other universal joint is attached between a nut socket and a sleeve having an extension coupling shaft receiving bore, said extension coupling shaft being selectively received in said sleeve shaft receiving bore, whereby said universal joint with attached sleeve and nut socket is selectively longitudinally movable with respect to said extension coupling shaft.

4. The U-bolt testing apparatus of claim 3, wherein said extension coupling shaft is square shaped in cross section and said sleeve receiving bore is square shaped in cross section.

5. The U-bolt testing apparatus of claim 3, further comprising a holding fixture for securely retaining a U-bolt during testing.

6. The U-bolt testing apparatus of claim 1, wherein said motors are hydraulic motors operating and driven by high pressure hydraulic fluid.

7. The U-bolt testing apparatus of claim 1, further comprising a computer connected to and controlling the torque output of said motors.

8. The U-bolt testing apparatus of claim 7, further comprising strain gauges on each of said U-bolt legs and connected to said computer, said computer recording the strain gauge outputs during testing.

9. The U-bolt testing apparatus of claim 1, wherein said motors are hydraulic motors operating and driven by high pressure hydraulic fluid.

10. An apparatus for testing U-bolts having a U-shaped body, a pair of legs having threaded ends and a nut on each of said threaded ends, said apparatus comprising:

a pair of motors, each motor having an output rotatable driven shaft;

a pair of spindles, each one of said spindles extending between one of said rotatable driven motor shafts and one of a pair of nuts threadingly received on a threaded end of a U-bolt;

wherein at least a portion of each of said spindles is selectively detachably attachable between said rotatably driven motor shafts and said U-bolt nuts; and, wherein said pair of motors are selectively simultaneously driven for selectively simultaneously rotatably driving said spindles, and wherein said U-bolt nuts are selectively simultaneously threadingly advanced on said U-bolt threaded ends.

11. The U-bolt testing apparatus of claim 10, further comprising a holding fixture for securely retaining a U-bolt during testing.

12. The U-bolt testing apparatus of claim 10, further comprising a computer connected to and controlling the torque output of said motors.

13. An apparatus for testing U-bolts having a U-shaped body, a pair of legs having threaded ends and a nut on each of said threaded ends, said apparatus comprising:
   a pair of motors, each motor having an output rotatably driven shaft;
   a pair of spindles, each one of said spindles extending between one of said rotatable driven motor shafts and one of a pair of nuts threadingly received on a threaded end of a U-bolt;
   wherein said pair of motors are selectively simultaneously driven for selectively simultaneously rotatably driving said spindles, and wherein said U-bolt nuts are selectively simultaneously threadingly advanced on said U-bolt threaded ends; and,
   a holding fixture for securely retaining a U-bolt during testing.

14. The U-bolt testing apparatus of claim 13, wherein said holding fixture includes a set of plates sandwiching a U-bolt, a stop member also sandwiched between said set of plates and located within said U-bolt, and a cap at one end of said plates having a pair of holes therethrough for receiving said U-bolt threaded ends therethrough, whereby threadingly advancing said nuts on said U-bolt threaded ends toward said cap places the U-bolt legs in tension.

15. The U-bolt testing apparatus of claim 14, further comprising a spacer between said cap and said plates, whereby a U-bolt having different leg lengths or different threaded ends length may be tested.

16. The U-bolt testing apparatus of claim 15, further comprising a stop member retaining pin selectively received through aligned holes in said plates and said stop member.

17. The U-bolt testing apparatus of claim 16, further comprising a second stop member retaining pin, also selectively received through aligned holes in said set of plates and said stop member.

18. The U-bolt testing apparatus of claim 1, further comprising a computer connected to and controlling the rotational speed and torque output of said motors.

19. The U-bolt testing apparatus of claim 18, further comprising strain gauges on each of said U-bolt legs and connected to said computer, said computer recording the strain gauge outputs during testing.

* * * * *

UNITED STATES PATENT AND TRADEMARK OFFICE
CERTIFICATE OF CORRECTION

PATENT NO. : 5,804,737
DATED     : September 8, 1998
INVENTOR(S) : Carl Johnson III, et al.

It is certified that error appears in the above-identified patent and that said Letters Patent is hereby corrected as shown below:

Col. 6, line 50, change "rotatable" to --rotatably--
Col. 6, line 53, change "rotatable" to --rotatably--
Col. 7, line 10, change "rotatable" to --rotatably--

Signed and Sealed this

Twenty-ninth Day of December, 1998

Attest:

BRUCE LEHMAN

Attesting Officer

Commissioner of Patents and Trademarks